United States Patent [19]

Friese et al.

[11] 4,373,631
[45] Feb. 15, 1983

[54] TAMPON PACK ESPECIALLY FOR A COATED TAMPON CONTAINING MEDICAMENTS

[75] Inventors: Axel Friese; Frantisek Simunek, both of Wuppertal, Fed. Rep. of Germany

[73] Assignee: Dr. Carl Hahn G.m.b.H., Dusseldorf, Fed. Rep. of Germany

[21] Appl. No.: 332,687

[22] Filed: Dec. 21, 1981

Related U.S. Application Data

[63] Continuation of Ser. No. 126,593, Mar. 3, 1980, abandoned.

[30] Foreign Application Priority Data

Apr. 24, 1979 [DE] Fed. Rep. of Germany ....... 2916564

[51] Int. Cl.³ ............. A61F 13/20; B65D 81/02; B65D 57/00
[52] U.S. Cl. ............................... 206/438; 128/285
[58] Field of Search ........... 206/438, 45.14, 45.19, 206/364, 463, 467, 469, 471, 480, 529, 530, 531; 128/285, 263; 220/306

[56] References Cited

U.S. PATENT DOCUMENTS

| | | | |
|---|---|---|---|
| 2,492,326 | 12/1949 | Scatti | 206/364 |
| 2,955,705 | 10/1960 | Krueger | 220/306 |
| 3,074,540 | 1/1963 | Beich | 206/469 |
| 3,358,686 | 12/1967 | Asaka | 206/438 |
| 3,444,991 | 5/1969 | Rsiybois | 206/530 |
| 3,473,646 | 10/1969 | Burke | 206/471 |
| 3,724,465 | 4/1973 | Duchane | 128/285 |
| 3,822,783 | 7/1974 | Martenson | 206/471 |

FOREIGN PATENT DOCUMENTS

| | | | |
|---|---|---|---|
| 112336 | 12/1968 | Denmark | 206/438 |
| 2617642 | 3/1977 | Fed. Rep. of Germany | 128/485 |
| 2729007 | 1/1979 | Fed. Rep. of Germany | 206/530 |

*Primary Examiner*—Herbert F. Ross
*Attorney, Agent, or Firm*—Jason Lipow

[57] ABSTRACT

A tampon pack is provided for containing a tampon of the type having a coated insertion end and an uncoated rear end. In accordance with the invention, a constriction is provided in that portion of the pack adapted to contain the rear end of the tampon and by virtue of this constriction, the insertion end of the tampon is held out of substantial contact with the container walls.

6 Claims, 5 Drawing Figures

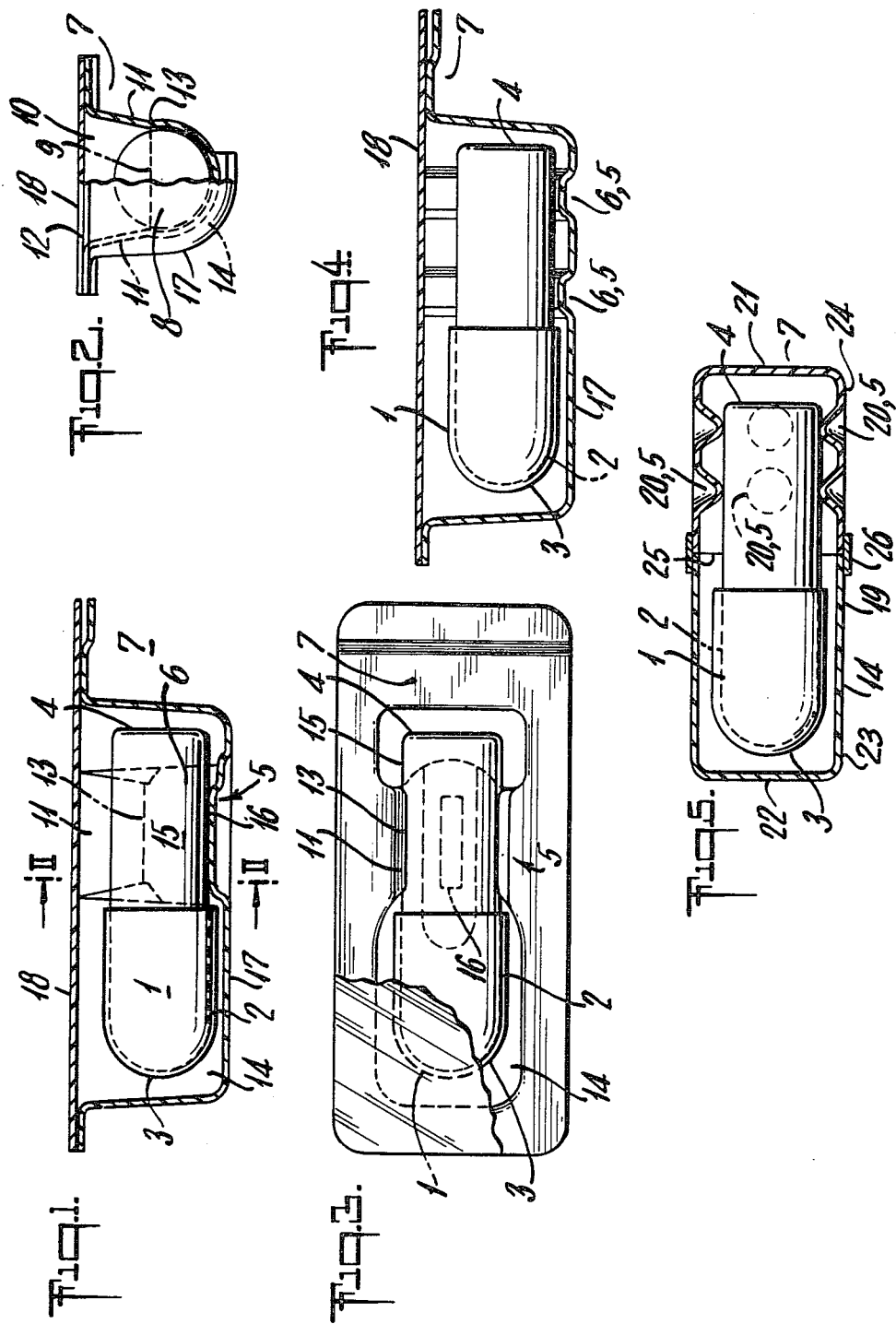

TAMPON PACK ESPECIALLY FOR A COATED TAMPON CONTAINING MEDICAMENTS

This is a continuation of application Ser. No. 126,593, filed Mar. 3, 1980, now abandoned.

BACKGROUND OF THE INVENTION

The invention relates to a tampon pack, in particular for female hygiene, having a constriction located in the rear zone of the tampon.

Recently, tampons have been marketed to an increasing extent, which have a coating or a covering at the insertion end. The coating can, for example, contain medicaments, diagnostic aids and/or lubricants for facilitating the insertion of the tampon. A problem in coated tampons of this type is the fact that the coating is frequently destroyed when it comes into contact with the packaging. Damage of this type can, for example, be caused by a purely mechanical contact with the packaging. Frequently, however, coatings of this type also have a relatively low softening point since they are intended preferably to melt or at least to soften at the body temperature so that, at unfavorable storage temperatures, parts of the coating can be transferred to the warmed packaging which is in contact with the coating.

It is the object of the invention to provide a tampon pack in which the insertion end of the tampon does not come into substantial contact with the pack.

SUMMARY OF THE INVENTION

According to the invention, this object is achieved where at least one constriction is provided on the packaging in the zone of the rear end of the tampon, which constriction holds the tampon in the pack in such a way that the insertion end of the tampon is not in substantial contact with the packaging.

The tampon packs which can be used here are cylindrical packs with an enveloping fold or flap, and in particular blister packs in which the constriction is located in the zone of the deep-drawn film.

The constrictions can have the form of annular beads, which extend transversely to the tampon and surround the tampon, or the form of individual hump-like projections. In blister packs, the annular beads are located on the deep-drawn film and surround more than half the circumference of the tampon, whilst in cylindrical packs these internal beads can completely surround the circumference of the tampon. Regarding the number and the arrangement of the constrictions, care must be taken to ensure that, as far as possible, the coated insertion end of the tampon is carried in free suspension, without substantial contact of the insertion end with the packaging occurring. The air space present between the coating and the packaging ensures good heat insulation and prevents premature softening of the coating, if the storage conditions are unfavorable.

BRIEF DESCRIPTION OF THE DRAWINGS

Preferred embodiments of the tampon packs according to the invention are illustrated in the drawings in which FIG. 1 shows a longitudinal section of a tampon blister pack with a bead-shaped constriction provided in the rear zone of the tampon;

FIG. 2 shows a partial cross-section II—II of the bead in FIG. 1;

FIG. 3 shows a plan view of the tampon blister pack of FIG. 1;

FIG. 4 shows a longitudinal section of a second embodiment of a tampon blister pack with two annular beads as constrictions; and FIG. 5 shows a longitudinal section of a cylindrical tampon pack with hump-like projections as constrictions.

DETAILED DESCRIPTION OF THE INVENTION

The tampon pack 7 according to FIG. 1 is designed as a blister pack. It contains a tampon 1 with a covering 2 at the insertion end 3. The covering 2 extends approximately over $\frac{1}{3}$ to $\frac{2}{3}$ and preferably approximately over one half of the total length of the tampon. The deep-drawn film 17 can preferably consist of polystyrene, a laminated film or polyvinyl chloride, and the cover film 18 sealed onto the deep-drawn film 17 can preferably consist of a metal foil, paper or a laminated film. In the rear, uncoated zone 4 of the tampon, a constriction 5, formed as a nip or internal bead 6, is provided on the deep-drawn film 17. This constriction 5 has a cross-section which essentially has the shape of a keyhole. This cross-section, which is shown in more detail in FIG. 2, essentially consists of an area in the form of a segment 8 of a circle, comprising more than half of the circle, and of a preferably isosceles trapezoid 10 placed on the imaginary secant 9 of the segment 8 of the circle. The imaginary secant 9 of the circle here coincides with the shorter parallel 9 of the trapezoid so that the walls 11 with essentially plane surfaces expand conically in the direction of the cover film 18. The longer parallel 12 of the trapezoid is formed by the cover film 18 of the blister pack. The height of the segment 8 of the circle is more than half and up to about $\frac{2}{3}$ of the diameter of the tampon. The edges 13 which are formed at the junction between the segment 8 of a circle and the trapezoid 10 and which protrude into the packing space, firmly hold the tampon 1 and prevent the covering 2 of the insertion end 3 of the tampon 1 from coming into contact with the pack 7. An air space 14 which ensures the requisite distance and the desired heat insulation, thus remains between the covering 2 and the pack 7. The diameter of the segment 8 of a circle approximately corresponds to the diameter of the tampon. The diameter of the segment 8 can also be somewhat smaller than the diameter of the tampon so that, after inserting the tampon into the pack, the rounded side walls 15 and the edges 13 are under tension and exert an additional clamping action on the tampon. Preferably, a recess 16 of rectangular cross-section is provided on that side of the segment 8 of a circle which is opposite the trapezoid 10. This recess 16 reduces the contact area of the tampon 1 with the packaging even in the rear zone 4 of the tampon, which is desired, for example, with regard to heat transfer from the pack 7 to the tampon 1. Preferably, the width of the constriction 5 is about $\frac{1}{4}$ to $\frac{1}{2}$ of the length of the tampon.

In the tampon blister pack shown in FIG. 4, two internal beads 6 are provided which, in cross-section, approximately have the form shown in FIG. 2. This embodiment has the effect of further reducing the contact area between the tampom 1 and the pack 7. The beads 6 are here at such a distance from one another that adequate fixing of the tampon 1 within the pack 7 is ensured. Preferably, the distance between these beads is about 1.0 to 2.0 cm.

The tampon pack 7 according to FIG. 5 consists of a cylindrical sleeve 19, on which several hump-like projections 20 are provided which project inwards and fix the tampon 1 in its position.

The cylindrical sleeve 19 consists, for example, of polyvinyl chloride, polystyrene, polypropylene or a laminated film. The packaging sleeve 19 consists of two parts 23, 24 and is closed at the two outer ends 21, 22. The joint edge 25 of the two parts 23, 24 is sealed by a tear strip 22. This embodiment is distinguished by a particularly small contact area between the tampon 1 and the packaging 7.

According to an embodiment, which is not illustrated, one or several internal beads 6 which surround the entire circumference of the rear zone 4 of the tampon can be provided in fully cylindrical tampon packs.

What is claimed is:

1. A tampon pack for containing and protecting a cylindrical tampon having a coated insertion end and an uncoated rear end, said pack walls provided with at least one constriction in the zone adapted to contain the rear end of the tampon whereby said tampon may be held with the coated insertion end out of substantial contact with the container walls; said tampon pack in the form of an elongated blister pack having a body portion and a cover wherein the transverse cross-section of the constriction is essentially in the form of a segment of a circle with a trapezoid placed thereon; said trapezoid having its shorter parallel side coincident with the imaginary secant of said segment, and its longer parallel side formed by the cover of the blister pack.

2. The tampon pack of claim 1 wherein the segment is a circle having a diameter about equal to or smaller than the diameter of the tampon.

3. The tampon pack of claim 2 wherein the segment is more than about one-half the area of the circle.

4. The tampon pack of claim 3 wherein the height of the segment is more than about one-half and less than about two-thirds the diameter of the tampon pack.

5. The tampon pack of claim 1 wherein the wall of the segment portion of the constriction opposite the trapezoid is provided with a recess having a rectangular cross-section.

6. The tampon pack of claim 1 wherein the width of the constriction is about from one-fourth to about one-half the length of the tampon.

* * * * *